US00PP10310P

United States Patent [19]

Sakazaki

[11] Patent Number: Plant 10,310

[45] Date of Patent: Mar. 31, 1998

[54] PETUNIA PLANT NAMED 'REVOLUTION PASTELPINK NO. 3'

[75] Inventor: Ushio Sakazaki, Hikone, Japan

[73] Assignee: Suntory Limited, Osaka, Japan

[21] Appl. No.: 746,557

[22] Filed: Nov. 13, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |
| P.P. 8,489 | 12/1993 | Hirabayashi et al. | Plt./68.1 |
| P.P. 8,768 | 6/1994 | Hirabayashi et al. | Plt./68.1 |
| P.P. 9,322 | 10/1995 | Tachibana et al. | Plt./68.1 |
| P.P. 9,341 | 10/1995 | Tachibana et al. | Plt./68.1 |
| P.P. 9,342 | 10/1995 | Sakazaki et al. | Plt./68.1 |
| P.P. 9,556 | 5/1996 | Tachibana et al. | Plt./68.1 |
| P.P. 9,557 | 5/1996 | Suzuki et al. | Plt./68.1 |

*Primary Examiner*—James R. Feyrer
*Assistant Examiner*—Elizabeth C. Kemmerer
*Attorney, Agent, or Firm*—Morgan & Finnegan; Eugene Moroz; Mary J. Morry

[57] ABSTRACT

Disclosed herein is a petunia plant, having a decumbent habit plant having long stems. The petunia plant has abundant branching and great profusion blooms, the whole bush remaining in bloom for a considerable period of time. The flowers are single and large, the petals having a strong purplish pink color with deep red purple lines radiating from a vivid yellow green bottom portion of the throat. The plant has a high resistance to rain, heat, drought, frost and pest, and the leaves and the flower petals have a strong resistance to rain and are not damaged during rainy season.

2 Drawing Sheets

BACKGROUND OF THE VARIETY

The present invention relates to a new and distinct variety of petunia plant obtained from mutant of "Revolution Purplepink" obtained from crossing a wild type of petunia plant (♀) native to Brazil and "Recoverer White (♂)".

The petunia is a very popular plant and is used for flower bedding and potting in the summer season. There are only a few varieties of the petunia plant which do not have an upright growth habit and which have a high resistance to rain, heat, cold, and diseases. The petunia which we previously filed, i.e., the "Revolution" series [(Revolution Purplepink (U.S. Pat. Plant No. 6,915), Revolution Brilliantpink (U.S. Pat. Plant No. 6,914), Revolution Brilliantpink-mini (U.S. Pat. No. Plant No. 6,899)] is decumbent type plant having long stems, a lower plant height, abundant branching, and a high resistance to heat, cold and rain. However, there are only a few varieties having a great profusion of flowers, pastel color flower petal and a high resistance to rain, heat, cold and diseases. Accordingly, this invention was aimed at obtaining a new variety having a pastel pink (strong purplish pink) color petal, together with the above features.

The new variety of petunia plant according to this invention originated from mutual occurring as a spontaneously generic variant of "Revolution Purplepink" (U.S. Pat. Plant No. 6,915) which we previously filed. The new variety of petunia plant was discovered in view of flower color during propagation of "Revolution Purplepink" in May, 1995. The discovered petunia plant was propagated by cutting from May, 1995 and then grown in bed and pot on trial from June, 1995. The botanical characteristics of the plant were examined, using similar variety, "Revolution Purplepink", for comparison. As a result, it was concluded that this petunia is distinguishable from any other variety, whose existence is known to us, sufficiently uniform and stable in its characteristics, then this new variety of petunia plant was named "Revolution Pastelpink No. 3".

In the following description, the color-coding is in accordance with The Horticultural Colour Chart of The Royal Horticultural Society, London, England (R.H.S. Colour Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

"Revolution Purplepink", the mutant parent of "Revolution Pastelpink No. 3", was obtained from crossing of a new wild type of petunia plant native to Brazil as the female parent and "Recoverer White" as the pollen parent, in June, 1985 at Yachiyo Farm of Keisei Rose Nurseries, Inc., residing at 755 Owadashinden, Yachiyo-shi, Chiba-ken, Japan.

The female parent use in the breeding of "Revolution Purplepink" was a wild type of petunia native to Brazil, the seeds of which were gathered in Gramado, Rio Grande Do Sul, Brazil and introduced to Japan in October, 1983. This wild type of petunia plant is presently maintained at the aforementioned the Yachiyo Farm of Keisei Rose Nurseries, Inc. and the Plant Biotechnology Laboratory of SUNTORY Ltd., residing at 863-1, Aza-Iketani, Oomori-cho, Youkkaitishi, Shiga-ken, Japan. The main botanical characteristics of this female parent of "Revolution Purplepink" are as follows.

Plant:

*Growth habit.*—Decumbent.

*Plant height.*—20 cm.

*Spreading area of plant.*—100–150 cm in diameter.

*Blooming period.*—May to August in the southern Kanto area, Japan.

Stem:

*Extending (length from base).*—50–80 cm.

*Thickness.*—Main stem 2.0–3.0 mm; lateral stem 1.5–2.5 mm.

*Pubescence.*—Many.

*Branching.*—Over-abundant.

*Length of internode.*—1.0–2.0 cm before blooming; 1.5–3.0 cm during blooming.

*Color.*—Strong yellow green (R.H.S. 144B-144C, JHS 3512-3513).

Leaf:

*Shape.*—Oval.

*Length.*—4.5–5.5 cm.

*Width.*—2.5–3.5 cm.

*Color.*—Grayish olive green (R.H.S. 137A-137B, JHS 3716-3717).

*Phyllotaxis.*—Opposite both before and during blooming.

*Pubescence.*—Few.

Flower:

*Facing direction.*—Opening obliquely upward.

*Type.*—Single.

*Shape.*—Funnel-shape, with five-fissured limb.

*Diameter.*—4.0–5.0 cm.

*Color.*—In the unopened stage (bud), dark reddish purple (R.H.S. 79B, JHS 8907-8909); when open, vivid reddish purple (R.H.S. 74A, JHS 9207), at full bloom, vivid reddish purple (R.H.S. 80A, JHS 8906).

*Reproductive organs.*—1 normal pistil and 5 normal stamens, both normal.

*Peduncle.*—0.9–1.2 mm in thickness, and 2.0–2.5 cm in length.

Physiological and ecological characteristics: High resistance to cold, relatively high resistance to heat, and moderate resistance to disease and pest.

"Recoverer White", used as the male parent in the breeding of variety of "Revolution Purplepink", is one of the Recoverer Series bred by the Sakata Seed Corp., Japan. The Recoverer Series includes "Recoverer Scarletred", "Recoverer Blue", and "Recoverer Pink", and these plants are commonly characterized by a high resistance to rain. The main botanical characteristics of "Recoverer White", are as follows.

Plant:

*Growth habit.*—Upright.

*Plant height.*—30–40 cm.

*Spreading area of plant.*—25–30 cm in diameter.

*Blooming period.*—April to September in the southern Kanto area, Japan.

Stem:

*Thickness.*—Main stem 5.0–7.0 mm; lateral stem 2.5–4.5 mm.

*Pubescence.*—Normal.

*Branching.*—Abundant.

*Length of internode.*—2.0–3.0 cm before blooming; 2.0–4.0 cm during blooming.

*Color.*—Strong yellow green (R.H.S. 144B-144C, JHS 3512-3513).

Leaf:

*Shape.*—Oval.

*Length(average).*—4.5–5.0 cm.

*Width(average).*—2.5–3.0 cm.

*Color.*—Strong yellow green to moderate olive green (R.H.S. 144A-146A, JHS 3507-3508).

*Phyllotaxis.*—Verticillate before blooming; opposite during blooming.

*Pubescence.*—Few.

*Thickness.*—0.4–0.6 mm.

Flower:

*Facing direction.*—Opening obliquely upward.

*Type.*—Single.

*Shape.*—Funnel-shape, with five-fissured limb.

*Diameter.*—8.0–8.5 cm.

*Color.*—In the unopened stage (bud), pale yellow green (R.H.S. 4D-157A, JHS 3304-3303); both when open and at full bloom, greenish white (R.H.S. 155D-155C, JHS 3701).

*Reproductive organs.*—1 normal pistil having a strong yellow green (144B-144C, JHS 3512) stigma, and 5 normal stamens each having a pale yellow (R.H.S. 161D, JHS 2503) anther and a greenish white (R.H.S. 157D, JHS 3501) filament.

*Peduncle.*—1.5–2.5 mm in thickness, and 2.5–3.0 cm in length.

*Physiological and ecological characteristics.*—High resistance to rain, heat, and disease, moderate resistance to pests.

And the botanical characteristics of the petunia plant "Revolution Purplepink" which is the mutant parent of this new variety "Revolution Purplepink No. 3" are as follows.

Plant:

*Growth habit.*—Decumbent. The stems hang down when potted in a hanging pot.

*Plant height.*—15–20 cm.

*Spreading area of plant.*—The stem extends to length of 50–80 cm from the base, and thus the spreading area of the plant is 100–150 cm in diameter.

*Growth.*—Very vigorous with abundant branching, a great profusion of blooms; the whole bush remaining in bloom for a considerable this period of time.

*Blooming period.*—Late March to late September in the southern Kanto area, Japan. The plant shape does not change throughout this period.

Stem:

*Thickness.*—Main stem 4.0–6.0 mm; lateral stem 2.0–3.0 mm.

*Pubescence.*—Normal.

*Branching.*—Over-abundant.

*Length of internode.*—1.0–1.5 cm before blooming; 3.0–4.0 cm during blooming.

*Color.*—Strong to moderate yellow green (R.H.S. 144B-143C, JHS 3512-3710).

Leaf:

*Shape.*—Lancet.

*Length(average).*—7.5–8.0 cm.

*Width(average).*—2.5–3.0 cm.

*Color.*—Moderate yellow green (R.H.S. 146B-137D, JHS 3508-3712).

*Phyllotaxis.*—Verticillate before blooming; opposite during blooming.

*Pubescence.*—Normal.

*Thickness.*—0.5–0.7 mm.

Flower:

*Facing direction.*—Opening obliquely upward.

*Type.*—Single.

*Shape.*—Funnel-shape, with five-fissured limb.

*Waving of petal.*—Week.

*Lobation of petal.*—Deep.

*Diameter.*—8.0–9.0 cm.

*Color.*—In the unopened stage (bud), deep to moderate purple (R.H.S. 86A-83A, JHS 8307-8306); when open, vivid reddish purple (R.H.S. 74A, JHS 9207), at full bloom, vivid reddish purple (R.H.S. 71D-74B, JHS 9206-9207), with strong reddish purple (R.H.S. 72B, JHS 9208) lines radiating from a small brilliant purple (R.H.S. 82C, JHS 8611) area closely proximate to a pale to light yellow green (R.H.S. 4D-151C, JHS 3310-3313) center portion. The small area completely surrounds the center portion. The reverse side of the petal is a light purple color (R.H.S. 75B, JHS 8903). The petal has a somewhat metallic luster.

*Reproductive organs.*—1 normal pistil having a grayish yellow green (R.H.S. 138A, JHS 3715) stigma, and 5 normal stamens each having a moderate blue (R.H.S. 98B-98C, JHS 8305) anther and a purple yellow green (R.H.S. 145D, JHS 3502) filament.

*Peduncle.*—2.0 mm in thickness, and 2.0–2.5 cm in length.

Physiological and ecological characteristics: High resistance to rain, heat, and drought. Also high resistance to disease, particularly gray mold (Botrytis). Moderate resistance to pests.

This new and distinct variety of petunia plant, "Revolution Pastelpink No. 3", was asexually reproduced by cutting at the aforementioned Plant Biotechnology Laboratory of SUNTORY Ltd., and the homogeneity and stability thereof were confirmed.

SUMMARY OF THE VARIETY

The new variety of petunia plant has a decumbent habit, long stems and strong purplish pink flower petal, and thus is very different from a similar variety, "Revolution Purplepink", parent of mutant. The plant has decumbent habit, abunant branching and great profusion blooms, and the whole bush remains in bloom for a considerable period of time. The flowers are single and large, and the petals having a strong purplish pink color, which is clearly distinguished from the vivid reddish purple of "Revolution Purplepink", with deep red purple lines radiating from a vivid yellow green bottom portion of throat. The plant has a high resistance to rain, heat, drought, frost and pest, especially to gray mold. The leaves, and flower petals have a strong resistance to rain and are not damaged during rainy season.

DESCRIPTION OF THE VARIETY

Figure 1:
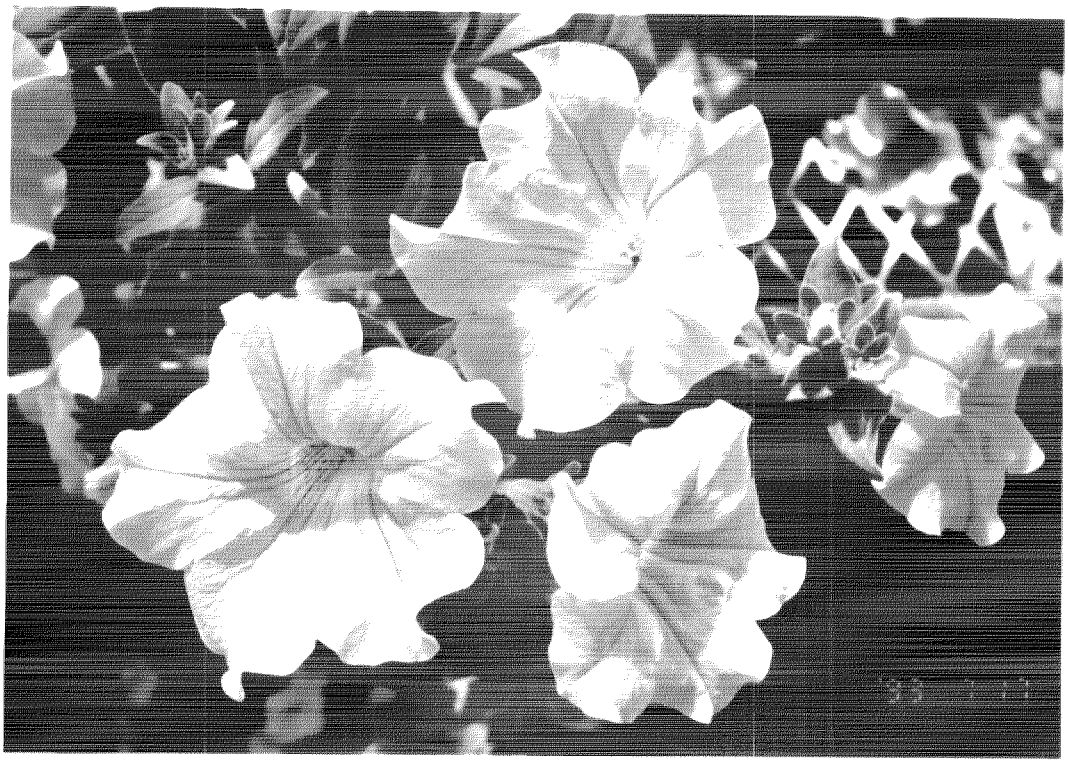
FIG. 1 is a photograph giving a partial view of the new variety of petunia plant planted in a flower pot.
Figure 2:
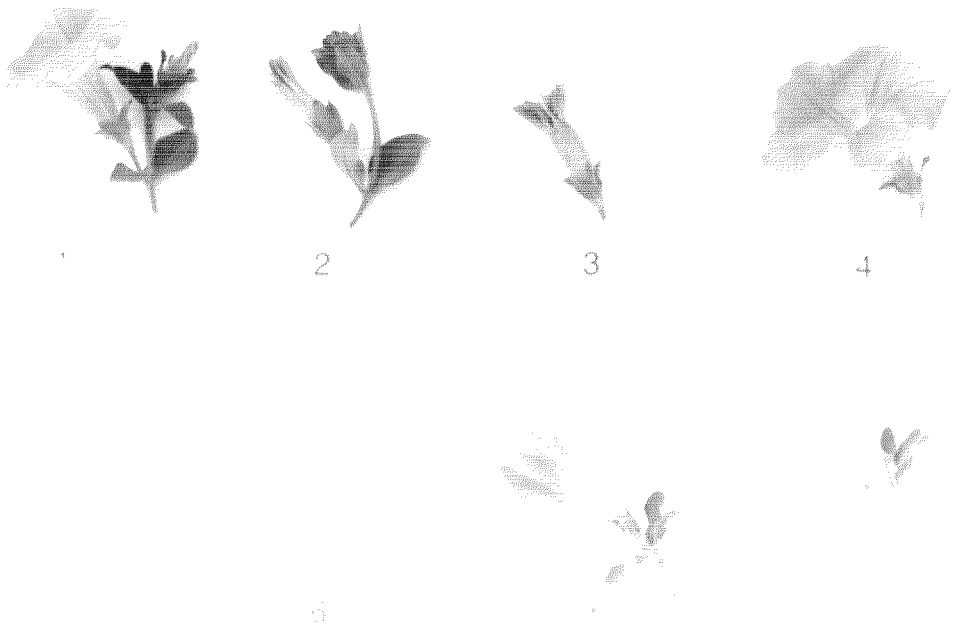
FIG. 2 is a photograph showing, in numerical order, a branch having an open flower(1), a current shoot(2), a bud(3), a side view of the flower(4), a front view of the flower(5), a rear view of the flower(6), an interior view of the flower(7), and pistil and stamen(8), of the new variety of petunia plant.

The botanical characteristics of the new and distinct variety of petunia plant "Revolution Pastelpink No. 3" are as follows.

*Growth habit.*—Decumbent. The stems hang down when potted in a hanging pot.

*Plant height.*—15–20 cm.

*Spreading area of plant.*—The stem extends to length of 50–70 cm from the base, and thus the spreading area of the plant is 100–150 cm in diameter.

*Growth.*—Very vigorous with abundant branching, a great profusion of blooms; the whole bush remaining in bloom for a considerable this period of time.

*Blooming period.*—Late March to late September in the southern Kanto area, Japan. The plant shape does not change throughout this period.

Stem:

*Thickness.*—4.0–6.0 mm.

*Pubescence.*—Normal.

*Branching.*—Over-abundant.

*Length of internode.*—3.0–4.0 cm.

*Color.*—Deep yellow green to vivid yellow green (R.H.S. 144A, JHS 3507-3506).

Leaf:

*Shape.*—Oval.

*Length.*—3.0–7.0 cm.

*Width.*—3.0–6.0 cm.

*Color.*—dark yellow green to dull green (R.H.S. 146A-145A, JHS 3508-3712).

*Thickness.*—0.5–0.7 mm.

*Phyllotaxis.*—Verticillate before blooming; opposite during blooming.

*Pubescence.*—Normal.

Flower:

*Facing direction.*—Opening obliquely upward.

*Type.*—Single.

*Shape.*—Funnel-shape, with five-fissured limb.

*Waving of petal.*—Week.

*Lobation of petal.*—Deep.

*Diameter.*—8.0–8.5 cm.

*Color.*—Strong purplish pink (R.H.S.61D-68D, JHS 8904) with deep red purple (R.H.S.77A, JHS 9209) lines radiating from a vivid yellow green (R.H.S. 144B, JHS 3105) bottom portion of throat. The outside of corolla tube is pale purplish pink (R.H.S.65D, JHS 8902).

*Reproductive organs.*—1 normal pistil and 5 normal stamens (2 stamens are higher the pistil).

Physiological and ecological characteristics: High resistance to rain, heat, drought, frost and pest, especially to gray mold. The leaves and flower petals have a strong resistance to rain and are not damaged during rainy season.

This new variety of petunia plant is most suitable for flower bedding and potting, particularly in hanging pots or planters, and further excellent for ground cover.

The plant of this new variety "Revolution Pastelpink No. 3" is presently planted and maintained at the Plant Biotechnology Laboratory of SUNTORY Ltd., residing at 863-1, Aza-Iketani, Oomori-cho, Youkaiti-shi, Shiga-ken, Japan.

I claim:

1. A new and distinct variety of petunia plant, substantially as herein illustrated and described, characterized particularly as to novelty by (A) being a decumbent habit plant having long stems, (B) an abundant branching and great profusion blooms, the whole bush remaining in bloom for a considerable period of time, (C) flowers are single and large, the petals having a strong purplish pink color with deep red purple lines radiating from a vivid yellow green bottom portion of throat, (D) a high resistance to rain, heat, drought, frost and pest, (E) leaves and flower petals have a strong resistance to rain and are not damaged during rainy season.

* * * * *